United States Patent [19]

Clewans

[11] 4,180,722

[45] Dec. 25, 1979

[54] LIQUID HEATING DEVICE

[76] Inventor: Bonnie Clewans, 214-05 23rd Ave., Bay Terrace, N.Y. 11360

[21] Appl. No.: 813,640

[22] Filed: Jul. 7, 1977

[51] Int. Cl.$^2$ ............................................. H05B 1/02
[52] U.S. Cl. .................................... 219/502; 219/497; 219/358; 128/272; 250/331; 250/226; 73/356
[58] Field of Search ............... 219/502, 497, 516, 358, 219/494; 73/356, 244; 99/281, 285, DIG. 10; 128/2 H, 214 A; 250/226, 331, 574–576; 15/11 A, DIG. 3; 356/43; 361/195

[56] References Cited

U.S. PATENT DOCUMENTS

| | | | |
|---|---|---|---|
| 2,640,137 | 5/1953 | Ketchledge | 219/502 |
| 2,792,484 | 5/1957 | Gurewitsch et al. | 219/502 |
| 2,814,202 | 11/1957 | Frans | 215/11 A |
| 2,856,885 | 10/1958 | Huyck et al. | 128/272 X |
| 3,200,301 | 8/1965 | Husband | 361/195 |
| 3,201,616 | 8/1965 | Houpt | 361/195 X |
| 3,486,694 | 12/1969 | Henson | 73/356 |
| 3,560,714 | 2/1971 | McDonald | 219/502 |
| 3,568,627 | 3/1971 | Selinger | 73/356 X |
| 3,591,810 | 7/1971 | Jackson | 73/356 X |
| 3,592,607 | 7/1971 | Bruce | 219/502 |
| 3,770,961 | 11/1973 | Westell | 250/331 |
| 3,867,040 | 2/1975 | Loffler et al. | 250/226 X |
| 3,882,363 | 5/1975 | Misencik | 219/502 |
| 4,016,761 | 4/1977 | Rozzell et al. | 128/2 H |
| 4,031,529 | 6/1977 | Borel et al. | 250/331 |
| 4,048,473 | 9/1977 | Burkhart | 219/389 |
| 4,076,979 | 2/1978 | Walter et al. | 250/226 |
| 4,087,687 | 5/1978 | Bean | 250/331 |
| 4,095,098 | 6/1978 | Looper | 250/575 |
| 4,125,330 | 11/1978 | Schild | 250/226 |

FOREIGN PATENT DOCUMENTS 1341735 of 1973 United Kingdom .................... 15/11 A Primary Examiner—Bruce A. Reynolds
Assistant Examiner—M. H. Paschall
Attorney, Agent, or Firm—Charles E. Temko

[57] ABSTRACT

A liquid heating device particularly adapted to the heating of sealed bottles containing liquids which are maintained in sterile condition until used, such as dialysates and the like. The device employs sealed bottles having a temperature sensitive element in intimate contact with the liquid being heated, which changes to a predetermined color and hue as the desired temperature is obtained. This color is compared with a color standard using a single source of light which is reflected against the indicator and the standard. The light reflected from these elements is photoelectrically compared, and the operation of the heating element is interrupted when a match is made. An independent timer interrupts said operation in the event of a failure of the photoelectric comparison.

4 Claims, 1 Drawing Figure

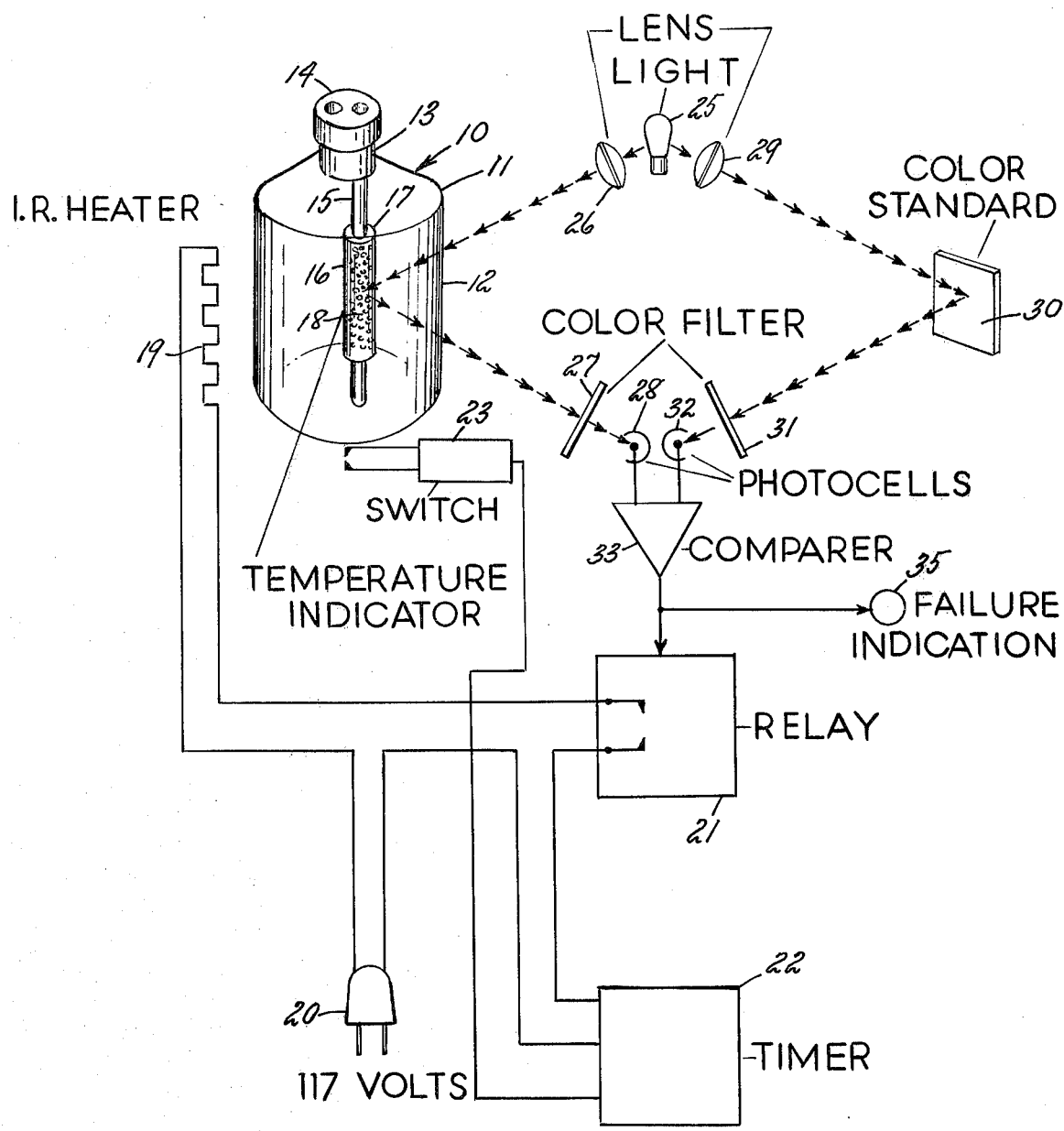

LIQUID HEATING DEVICE

BACKGROUND OF THE INVENTION

This invention relates generally to the field of container heating devices, and more particularly to an improved device for heating contents in sealed containers, particularly where the contents are for surgical use.

In many medical procedures, such as peritoneal dialysis, a sterile fluid (dialysate) must be heated to a specific temperature, e.g. the normal body temperature of the patient. This is currently accomplished by immersing the sealed glass container with the dialysate in a water bath, the temperature of which is thermostatically controlled. Reliance is placed on eventual temperature stabilization between the heated water and the sealed sterile dialysate through the glass container. In order to be certain that this temperature stabilization is effective, the dialysate container must be immersed for a relatively long period. Even after several hours, the temperature of the internal dialysate cannot be measured. One possible improvement would be the addition of a sterilized thermometer inserted during the production of the dialysate. However, such a course has accompanying drawbacks, such as poor readibility, the possibility of accidental thermometer breakage and resultant contamination, as well as the fact that the thermometer can be damaged in the event that the range of the thermometer is exceeded.

The prior art does not offer any device whereby it is possible to know the core temperature of a fluid in a readily visible and accurate fashion.

SUMMARY OF THE INVENTION

Briefly stated, the invention contemplates the provision of an improved device for heating sterile bottles using an externally disposed infrared heating element. It employs a temperature sensitive liquid crystal material sealed in an appropriate transparent medium. Such crystal materials are presently commercially available, and selectively reflect portions of the visible spectrum in accordance with their temperature. A typical such material may have a range of a few degrees, and reflect a given color or hue at a very specific temperature. By using several different such materials, it is possible to accurately indicate, by color, the core temperature of the fluid. The material may be masked to allow numerals to appear upon reaching a specific temperature or temperatures. In the case of peritoneal dialysis, this ability permits a nurse to know when the fluid has reached acceptable body temperature (37° C.). It also tends to prevent the instillation of a fluid which is above or below body temperature, and thereby avoid many actual and potential problems in the management of the patient being dialyzed. Temperature control by automatic means is readily achieved with a beam of light passed through the sealed container, transparent fluid and reflected from the liquid crystal temperature sensor. A color filter and photocell perform the same function as the human eye in determining when the desired temperature has been reached. To insure accurate reliable and fail-safe operation, conventional electronic techniques to compare the color and hue of the sensor with a color standard are used, so that power to the heating element may be interrupted when a match is found.

BRIEF DESCRIPTION OF THE DRAWING

In the drawing, to which reference will be made in the specification, the single FIGURE is a schematic view in perspective of an embodiment of the invention.

DETAILED DESCRIPTION OF THE DISCLOSED EMBODIMENT

In accordance with the invention, the device, generally indicated by reference character 10 includes a sterile bottle 11 having a main body 12 and a neck supporting a stopper 14. The stopper mounts an air inlet tube 15 supporting a temperature sensitive element 16 in the form of a hollow sleeve 17. The sleeve 17 is hollow, and encases known liquid crystals 18 of formulation capable of displaying a particular hue or color upon the attainment of a predetermined temperature, as for example body temperature.

In use, the bottle 11 is placed adjacent to a known type infrared heater element 19 connected to a source of power at 20. Power is supplied through a relay 21 in series with an electronic timer 22 of known type and a pressure operated switch 23 actuated by the weight of a bottle 11 thereupon.

Operation of the relay is such that the contacts thereof close when the switch 23 is closed, and open when the contents of the bottle 11 attain predetermined temperature.

This is accomplished by the provision of a single light source 25, part of the beam output of which passes through a first lens 26 to fall upon the indicator 18, from which it is reflected through a first color filter 27 to fall upon the light sensitive component of a first photocell 28. Another portion of the beam output of the light source 25 passes through a second lens 29, to be reflected from a surface 30 bearing a color standard, through a second filter 31 to fall upon the light sensitive element of a second photocell 32.

The outputs of the photocells 28 and 32 are fed to an operational amplifier 33 which functions as a comparer. As long as the color of the indicator 18 differs from that of the color standard 30, there will be a net output from the comparer 33, the voltage being used to maintain the contacts of the relay 21 in closed condition, so that power continues to flow to the heater element 19. When a match is found between the voltages of the photocells, the net output of the comparer vanishes, and this fact is used to open the contacts of the relay, thereby interrupting the flow of power to the heater. This net voltage may also be used to illuminate a light emitting diode 35, the extinguishment of which indicates that the desired temperature of the contents of the bottle has been obtained, and the failure to illuminate when a bottle is positioned in heating position serving to indicate that the comparer 33 is not operating properly.

The electronic timer 22 of known type is actuated each time the pressure switch is closed, and is set to time a period somewhat greater than that normally required during proper operation, so that in the event of the failure of the comparer structure, the operation of the heater element will be interrupted before the bottle is substantially overheated.

I wish it to be understood that I do not consider the invention limited to the precise details of structure shown and set forth in this specification, for obvious modifications will occur to those skilled in the art to which the invention pertains.

I claim:

1. As a new article of manufacture, a transparent bottle for containing surgical dialysate and similar fluids comprising: a main body defining a cavity for the holding of said fluid, a neck portion communicating with said cavity, a stopper selectively engageable within said necked portion, an air inlet tube supported by said stopper, a hollow transparent sleeve carried by a segment of said air inlet tube, and a color variable temperature sensitive means including a quantity of temperature sensitive liquid crystals carried by said sleeve and visible through said body.

2. In combination, a bottle as set forth in claim 1, and a device for selectively heating said bottle comprising: an electrically powered radiant heating element in the area of said bottle, and means in series with said heating element for interrupting power to said heating element upon the attainment of a predetermined temperature indicated by said variable temperature sensitive indicating means.

3. The combination as set forth in claim 2, further comprising: a single light source, a pair of photocells, means reflecting one portion of the beam output of said single light source upon said indicator means, and a second portion of the beam output of said light source upon a color standard to cause each portion to fall upon one of said pair of photocells; comparer means receiving and comparing the output of said photocells and interrupting the operation of said heater element when a match is obtained.

4. The combination as set forth in claim 3, further characterized in the provision of means overriding said comparer means and operative to interrupt operation of said heating element in the event of failure of said comparer means.

* * * * *